United States Patent
Irisawa et al.

(10) Patent No.: US 10,568,603 B2
(45) Date of Patent: Feb. 25, 2020

(54) PHOTOACOUSTIC MEASUREMENT DEVICE AND PUNCTURE NEEDLE

(71) Applicant: FUJIFILM Corporation, Minato-ku, Tokyo (JP)

(72) Inventors: Kaku Irisawa, Ashigarakami-gun (JP); Kazuhiro Tsujita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 511 days.

(21) Appl. No.: 14/817,363

(22) Filed: Aug. 4, 2015

(65) Prior Publication Data

US 2015/0335289 A1  Nov. 26, 2015

Related U.S. Application Data

(63) Continuation of application No. PCT/JP2014/056874, filed on Mar. 14, 2014.

(30) Foreign Application Priority Data

Mar. 22, 2013 (JP) .................................. 2013-059670
Mar. 10, 2014 (JP) .................................. 2014-045922

(51) Int. Cl.
*A61B 8/08* (2006.01)
*A61B 17/34* (2006.01)
(Continued)

(52) U.S. Cl.
CPC ........ *A61B 8/0841* (2013.01); *A61B 17/3403* (2013.01); *A61B 5/0095* (2013.01);
(Continued)

(58) Field of Classification Search
CPC .. A61B 5/00; A61B 8/00; A61B 17/00; A61B 2090/00; A61B 5/6848;
(Continued)

(56) References Cited

U.S. PATENT DOCUMENTS 3,657,181 A * 4/1972 Riedesel ................ G10K 11/30
                                                    106/270
4,566,438 A * 1/1986 Liese ..................... A61B 5/6848
                                                    600/129

(Continued)

FOREIGN PATENT DOCUMENTS

JP  2009-31262 A  2/2009
JP  2013-13713 A  1/2013

OTHER PUBLICATIONS

Su, Jimmy L., et al. "Photoacoustic imaging of clinical metal needles in tissue." Journal of biomedical optics 15.2 (2010): Feb. 13, 2009.*

(Continued)

*Primary Examiner* — Luther Behringer
*Assistant Examiner* — Sean D Mattson
(74) *Attorney, Agent, or Firm* — Birch, Stewart, Kolasch & Birch, LLP

(57) ABSTRACT

A photoacoustic measurement device having a puncture needle, where the puncture needle 14 is a hollow needle that has an opening formed at a tip thereof. The puncture needle 14 includes a puncture needle body 31 and a light guide 32. The light guide 32 extends in a longitudinal direction of the puncture needle body. The light guide 32 emits light at least in part to the puncture needle body 31 while guiding light emitted from a light source toward the tip of the puncture needle body.

6 Claims, 9 Drawing Sheets

(51) Int. Cl.
  *A61B 5/00* (2006.01)
  *A61B 90/30* (2016.01)
  *A61B 90/00* (2016.01)
  *A61B 5/06* (2006.01)
  *G01N 21/17* (2006.01)
  *G01N 29/24* (2006.01)

(52) U.S. Cl.
  CPC ............ *A61B 5/061* (2013.01); *A61B 5/6848* (2013.01); *A61B 2090/306* (2016.02); *A61B 2090/3945* (2016.02); *G01N 21/1702* (2013.01); *G01N 29/2418* (2013.01); *G01N 2201/067* (2013.01); *G01N 2201/106* (2013.01)

(58) Field of Classification Search
  CPC . A61B 5/0095; A61B 8/0841; A61B 17/3403; A61B 2090/306; A61B 2090/3945
  See application file for complete search history.

(56) References Cited

U.S. PATENT DOCUMENTS

| | | | | |
|---|---|---|---|---|
| 5,280,788 A * | 1/1994 | Janes | ............... | A61B 5/0084 600/476 |
| 6,143,018 A * | 11/2000 | Beuthan | ............ | A61B 18/24 604/20 |
| 6,564,087 B1 * | 5/2003 | Pitris | ............... | A61B 1/00172 600/478 |
| 6,641,555 B1 * | 11/2003 | Botich | ............... | A61M 5/158 604/110 |
| 2002/0047058 A1 * | 4/2002 | Verhoff | ............... | A61K 9/14 241/26 |
| 2004/0019297 A1 * | 1/2004 | Angel | ............... | A61B 10/04 600/564 |
| 2005/0267555 A1 * | 12/2005 | Marnfeldt | .......... | A61B 17/3417 607/116 |
| 2009/0190883 A1 * | 7/2009 | Kato | ............... | A61B 5/0066 385/33 |
| 2009/0323076 A1 * | 12/2009 | Li | ............... | A61B 5/0066 356/479 |
| 2010/0016844 A1 * | 1/2010 | Patel, Jr. | ............ | A61B 90/30 606/15 |
| 2010/0174197 A1 | 7/2010 | Nakajima et al. | | |
| 2012/0253180 A1 * | 10/2012 | Emelianov | ........... | A61B 8/0841 600/424 |
| 2013/0096422 A1 * | 4/2013 | Boctor | ............ | A61B 5/0095 600/424 |
| 2014/0378796 A1 * | 12/2014 | Chen | ............... | A61B 5/6848 600/328 |

OTHER PUBLICATIONS

International Search Report, issued in PCT/JP2014/056874, dated Apr. 8, 2014.
Written Opinion of the International Searching Authority, issued in PCT/JP2014/056874, dated Apr. 8, 2014.

* cited by examiner

PHOTOACOUSTIC MEASUREMENT DEVICE AND PUNCTURE NEEDLE

CROSS-REFERENCE TO RELATED APPLICATIONS

This application is a Continuation of PCT International Application No. PCT/JP2014/056874 filed on Mar. 14, 2014, which claims priority under 35 U.S.C § 119(a) to Japanese Patent Application No. 2013-059670 filed on Mar. 22, 2013 and Japanese Patent Application No. 2014-045922 filed on Mar. 10, 2014. Each of the above application(s) is hereby expressly incorporated by reference, in its entirety, into the present application.

BACKGROUND OF THE INVENTION

1. Field of the Invention

The present invention relates to a photoacoustic measurement device, and more particularly, to a photoacoustic image generating device that generates a photoacoustic image on the basis of photoacoustic waves generated due to the emission of light after light is emitted to a subject. Further, the invention relates to a puncture needle that is used for the photoacoustic image generating device.

2. Description of the Related Art

An ultrasonic inspection method is known as one kind of image inspecting method that can inspect the internal state of a living body in a non-invasive manner. An ultrasonic probe, which can transmit and receive ultrasonic waves, is used for ultrasonic inspection. When ultrasonic waves are transmitted to a subject (living body) from the ultrasonic probe, the ultrasonic waves travel in the living body and are reflected by a tissue interface. When a distance is calculated on the basis of a time until the reflected ultrasonic waves return to the ultrasonic probe after the reflected ultrasonic waves are received by the ultrasonic probe, an image of the inner state of the living body can be made.

Further, photoacoustic imaging, which makes an image of the inside of a living body by using a photoacoustic effect, is known. In general, the inside of the living body is irradiated with pulsed laser light, such as laser pulses, in photoacoustic imaging. In the living body, biological tissue absorbs the energy of the pulsed laser light and ultrasonic waves (photoacoustic waves) are generated due to adiabatic expansion caused by the energy. When the photoacoustic waves are detected by an ultrasonic probe or the like and a photoacoustic image is formed on the basis of detection signals, the inside of the living body can be made visible on the basis of the photoacoustic waves.

Here, a combination of biological information imaging using photoacoustic waves and treatment using a puncture needle is mentioned in JP2009-31262A. In JP2009-31262A, a photoacoustic image is generated and is observed to find an affected part, such as a tumor, a portion that is suspected as an affected part, and the like. In order to more closely inspect such a portion or in order to perform injection or the like on an affected part, cells are taken or injection is performed on an affected part by using an injection needle, or a puncture needle such as a cytodiagnosis needle. In JP2009-31262A, it is possible to insert a needle to an affected part while observing the affected part, by using a photoacoustic image.

SUMMARY OF THE INVENTION

In the photoacoustic imaging, the irradiation of light to a subject is generally performed on the surface of the subject. Particularly, when a tip of a puncture needle is stuck to a deep position, light applied from the surface of the subject does not sufficiently reach the puncture needle that is stuck to the deep position. For this reason, it is difficult to confirm the position of the puncture needle by using a photoacoustic image. For this problem, JP2013-013713A discloses that a puncture needle is provided with a light emitting portion and light is emitted from the light emitting portion. The light emitting portion is formed of, for example, a light guide member that is formed so as to have a thickness reduced toward the tip of the puncture needle.

In JP2013-013713A, light is emitted from the light emitting portion after the puncture needle is stuck into the subject, and photoacoustic waves, which are generated when a light absorber present in the subject absorbs the light emitted from the light emitting portion of the puncture needle, are detected. A photoacoustic image is generated on the basis of the photoacoustic waves. In JP2013-013713A, it is possible to confirm a position where the puncture needle is present since it is possible to confirm a position, to which the light emitted from the light emitting portion is irradiated, in the photoacoustic image. However, in JP2013-013713A, light is emitted to the subject from the light emitting portion and a member generating photoacoustic signals is the light absorber present in the subject. For this reason, there is a case in which it is difficult to confirm the position of the needle.

The invention has been made in consideration of the above-mentioned problems, and an object of the invention is to provide a photoacoustic image generating device that can confirm the position of a puncture needle in a photoacoustic image even in the case where the puncture needle is stuck to a deep position from the surface of a subject.

Further, an object of the invention is to provide a puncture needle that is used for the photoacoustic image generating device.

In order to achieve the object, the invention provides a puncture needle including a hollow puncture needle body that has an opening formed at a tip thereof, and a light guide that extends in a longitudinal direction of the hollow puncture needle body and emits light at least in part to the hollow puncture needle body while guiding light emitted from a light source toward the tip of the hollow puncture needle body.

In the invention, the light guide may be disposed outside the hollow puncture needle body.

In the invention, the puncture needle may further include a tube that covers the hollow puncture needle body and the light guide. The tube covering the light guide may be made of, for example, a fluorine resin.

Instead, the light guide may be disposed in the hollow puncture needle body.

The light guide may be bonded to the hollow puncture needle body by an adhesive having light absorbency.

The light guide may include an optical fiber of which a clad of at least a part of a portion coming into contact with the hollow puncture needle body is removed. In this case, the clad may be removed at a plurality of locations in an extension direction. Further, the clad may be removed at predetermined intervals.

The optical fiber included in the light guide may be a part of an optical wire that guides light emitted from a light source to the puncture needle.

Further, the invention provides a photoacoustic image generating device including: a light source; the puncture needle; an acoustic wave detecting part for detecting a photoacoustic wave generated in a subject after the light is emitted from the light guide; and a photoacoustic image generating part for generating a photoacoustic image on the basis of a detection signal of the photoacoustic wave.

In the photoacoustic image generating device of the invention, the puncture needle is provided with the light guide that extends in the longitudinal direction of the hollow puncture needle body and emits light at least in part to the hollow puncture needle body while guiding light emitted from the light source toward the tip of the hollow puncture needle body. In the invention, light is emitted to the hollow puncture needle body from the light guide in the longitudinal direction of the puncture needle and photoacoustic waves are generated from a portion, to which light is irradiated, of the hollow puncture needle body. Since the puncture needle is provided with the light guide that emits light, photoacoustic waves can be generated at the puncture needle even when the puncture needle is stuck to a deep position from the surface of a subject. Since a photoacoustic image is generated on the basis of detected photoacoustic waves, it is possible to confirm the position of the puncture needle.

DESCRIPTION OF THE PREFERRED EMBODIMENTS

Figure 1:
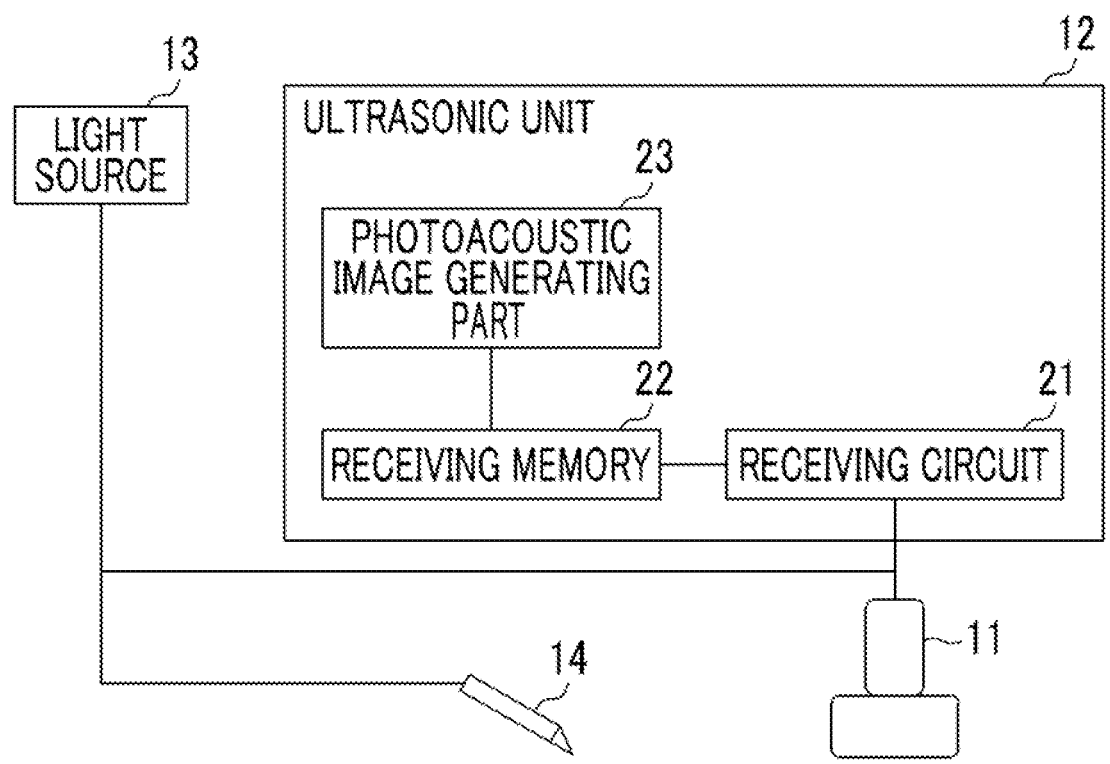
FIG. 1 is a block diagram showing a photoacoustic image generating device according to a first embodiment of the invention.

Embodiments of the invention will be described below in detail with reference to the drawings. FIG. 1 shows a photoacoustic image generating device according to a first embodiment of the invention. The photoacoustic image generating device 10 includes a probe (ultrasonic probe) 11, an ultrasonic unit 12, and a light source unit 13. Meanwhile, an ultrasonic wave is used as an acoustic wave in the embodiment of the invention, but the acoustic wave is not limited to the ultrasonic wave. As long as an appropriate frequency is selected according to a subject, measurement conditions, or the like, an acoustic wave having an audio frequency may be used.

The light source unit (light source) 13 is formed of, for example, a laser light source. The light source unit 13 includes a solid-state laser using, for example, YAG (yttrium.aluminum.garnet), alexandrite, or the like. Laser light emitted from the light source unit 13 is guided to a puncture needle 14 by light guide means such as an optical fiber. Further, laser light emitted from the light source unit 13 is guided to a probe 11 by an optical fiber or the like.

Figure 2A:
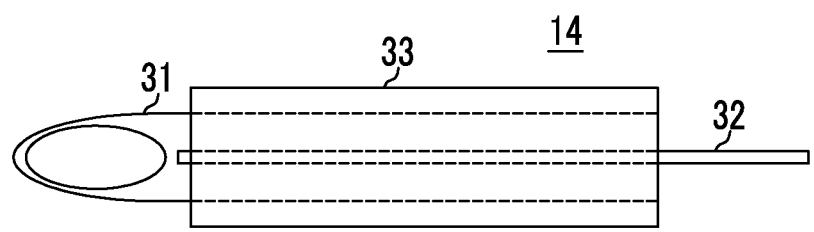
FIG. 2A is a top view of a puncture needle used in the first embodiment and FIG. 2B is a sectional view of a central portion of the puncture needle.
Figure 2B:
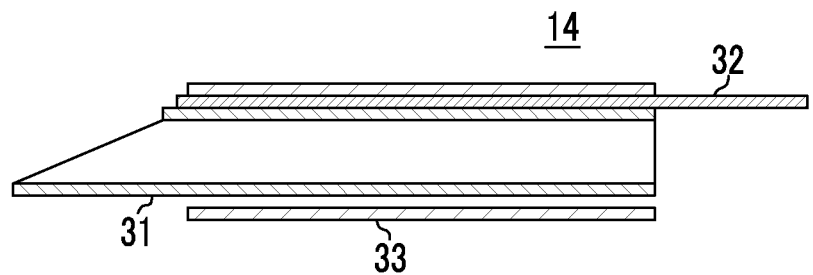

The puncture needle 14 is a needle that is stuck into a subject. FIG. 2A is a top view of the puncture needle 14 that is seen from above, and FIG. 2B is a sectional view of a central portion. The puncture needle 14 has a puncture needle body 31, a light guide 32, and a tube 33. The puncture needle body 31 has an opening formed at the tip thereof and is formed in a hollow shape. The puncture needle body 31 is formed by rounding, for example, a metal plate and obliquely cutting the rounded metal plate at a tip portion thereof. After the puncture needle body 31 is formed, the light guide 32 is mounted on the outer wall of the short portion (short side) of the puncture needle body 31 of which the tip portion has been cut obliquely.

The light guide 32 extends in the longitudinal direction of the puncture needle body 31. The light guide 32 is made of, for example, high refractive index glass, a resin, or the like. The light guide 32 is optically connected to a light emitting end of an optical fiber that guides light emitted from, for example, the light source unit 13 (see FIG. 1) to the puncture needle 14. While guiding light emitted from the light source unit 13 toward the tip of the puncture needle body 31, the light guide 32 emits light at least in part to the puncture needle body 31. In FIGS. 2A and 2B, the light guide 32 emits light toward the puncture needle body 31 over the entire puncture needle body 31 in the longitudinal direction. The light guide 32 is disposed outside the hollow puncture needle body 31.

The tube 33 is a hollow tube that covers the puncture needle body 31 and the light guide 32. The tube 33 is made of a fluorine resin such as PTFE (polytetrafluoroethylene). The diameter of the tube 33 is slightly larger than, for example, the diameter (outer diameter) of the puncture needle body 31. The tube 33 has a property that allows acoustic waves to be transmitted. Meanwhile, FIG. 2B shows an example in which the tube 33 is disposed so that the center of the puncture needle body 31 corresponds to the center of the tube 33, but the center of the puncture needle body 31 and the center of the tube 33 do not need to correspond to each other. For example, the puncture needle body 31 and the tube 33 may come into contact with each other on the side opposite to the side of the puncture needle body 31 on which the light guide 32 is provided.

Returning to FIG. 1, the probe 11 is acoustic wave detecting part, and has, for example, a plurality of ultrasonic vibrators that are arranged one-dimensionally. The probe 11 detects photoacoustic waves that are generated in the subject. The photoacoustic waves, which are detected by the probe 11, include photoacoustic waves that are generated due to light emitted from the probe 11 and photoacoustic waves that are generated in the puncture needle body 31 due to light emitted from the light guide 32 (see FIGS. 2A and 2B) of the puncture needle 14. The probe 11 not only may detect the photoacoustic waves but also may output acoustic waves (ultrasonic waves) to the subject and may detect reflected acoustic waves (reflected ultrasonic waves) of the transmitted ultrasonic waves reflected from the subject.

The ultrasonic unit 12 includes a receiving circuit 21, a receiving memory 22, and a photoacoustic image generating part 23. The receiving circuit 21 receives detection signals (photoacoustic signals) of the photoacoustic waves that are detected by the probe 11. The received photoacoustic signals are converted into digital signals by an AD converter (analog to digital converter) (not shown) or the like and are stored in the receiving memory 22. The photoacoustic image generating part 23 reads photoacoustic signals out of the receiving memory 22, and generates a photoacoustic image on the basis of the photoacoustic signals. The generation of the photoacoustic image includes image reconstruction, such as phase matching addition, detection, logarithmic transformation, and the like. The generated photoacoustic image is displayed on image display means (not shown) such as a display. The ultrasonic unit 12 may further include ultrasound image generating means for generating an ultrasound image on the basis of the detection signals (reflected ultrasonic wave signals) of the reflected ultrasonic waves detected by the probe 11.

The puncture needle 14 is stuck into the subject from, for example, the surface of the subject by a doctor or the like. After the puncture needle 14 is stuck into the subject, laser light is emitted from the light source unit 13. Light emitted from the light source unit 13 is incident on the light guide 32 through an optical fiber or the like. The light, which is incident on the light guide 32, is guided toward the tip of the puncture needle body 31 by the light guide 32. At this time, light leaking out of the light guide 32 is irradiated to the puncture needle body 31. Photoacoustic waves, which are caused by light emitted from the light guide 32, are generated in the puncture needle body 31.

Further, light emitted from the light source unit 13 is guided to the probe 11 and is emitted from the probe 11 toward the subject. Photoacoustic waves, which are caused by light emitted from the probe 11, are generated in the subject.

Meanwhile, the emission of light to the subject does not necessarily need to be performed from the probe 11 and the emission of light may be performed from a portion other than the probe 11. Furthermore, the emission of light from the probe 11 and the emission of light from the light guide of the puncture needle 14 do not necessarily need to be performed at the same time, and may be separately performed. Moreover, the same light source does not need to be used for the emission of light from the probe 11 and the emission of light from the light guide of the puncture needle 14, and a light source used for the emission of light to the probe 11 and a light source used for the emission of light to the light guide of the puncture needle 14 may be separately provided. The wavelength of light emitted from the probe 11 and the wavelength of light emitted from the light guide 32 do not need to be equal to each other, and may be set to wavelengths different from each other.

The probe 11 detects photoacoustic waves that are generated in the subject due to the irradiation of laser light. The receiving circuit 21 receives photoacoustic signals from the probe 11, and the photoacoustic signals are stored in the receiving memory 22. The photoacoustic image generating part 23 generates a photoacoustic image on the basis of photoacoustic signals. The imaging of the distribution of light absorbers and a portion of the puncture needle body 31, which are present in the subject, is performed using the photoacoustic image. The generated photoacoustic image is displayed on the image display means or the like.

In this embodiment, the puncture needle 14 is provided with the light guide 32 that extends in the longitudinal direction of the puncture needle body 31 and emits light to the puncture needle body 31 while guiding light emitted from the light source unit 13 toward the tip of the puncture needle body. By irradiating light to the puncture needle body 31 from the light guide 32 in the longitudinal direction of the puncture needle body 31, photoacoustic waves can be generated in the puncture needle body 31 even though the puncture needle 14 is stuck to a deep position and light irradiated from the surface of the subject does not reach the puncture needle 14. Further, since light is irradiated from the light guide 32 over the entire puncture needle body 31 in the longitudinal direction, photoacoustic waves can be generated from the entire elongated puncture needle 14. By generating a photoacoustic image on the basis of detected photoacoustic waves, the imaging of the puncture needle 14 can be performed using the photoacoustic image. Accordingly, it is possible to confirm the position of the puncture needle.

Furthermore, in this embodiment, the puncture needle body 31 and the light guide 32 are covered with the tube 33. By the tube 33 covering the light guide 32, the light guide 32 can be solidly fixed to the puncture needle body 31. Photoacoustic waves, which are generated in the puncture needle body 31, are propagated to the subject through the tube 33. Since the tube 33 made of a fluorine resin is present between the puncture needle body 31 made of metal and the subject (water), it is possible to reduce a difference in acoustic impedance between metal and water. Accordingly, it is possible to easily transmit photoacoustic waves, which are generated in the puncture needle body 31, to the subject. Moreover, since the tube 33 is made of a fluorine resin, it is possible to improve the sliding of the surface of the needle in comparison with a case in which the puncture needle body 31 is directly stuck into the subject.

Figure 3A:
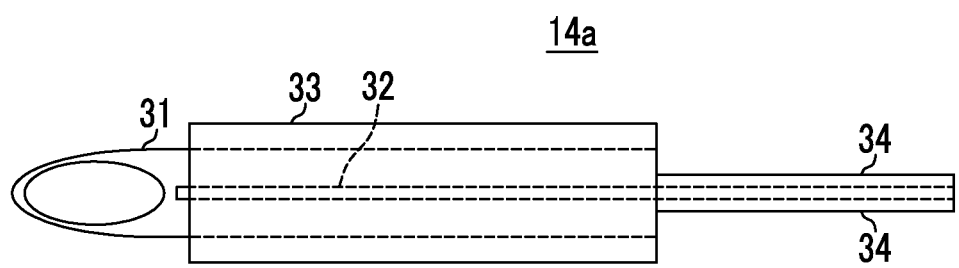
FIG. 3A is a top view of a puncture needle used in a second embodiment of the invention and FIG. 3B is a sectional view of a central portion of the puncture needle.
Figure 3B:
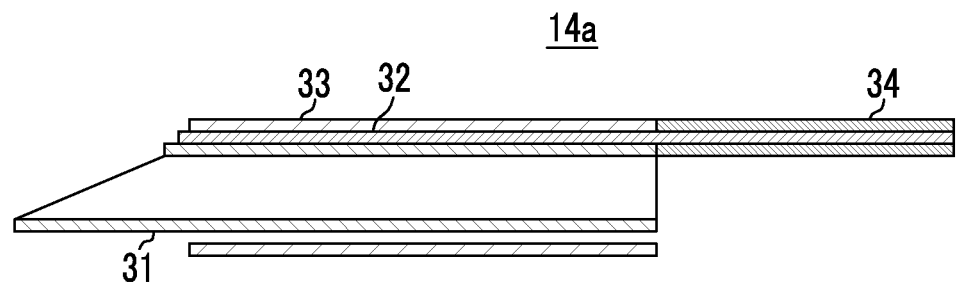

Subsequently, a second embodiment of the invention will be described. FIG. 3A is a top view of a puncture needle used in the second embodiment of the invention and FIG. 3B is a sectional view of a central portion of the puncture needle. In a puncture needle 14a of this embodiment, a light guide 32 is formed of an optical fiber from which a clad 34 has been removed. Further, the optical fiber is a part of an optical wire that guides light emitted from the light source unit 13 to the puncture needle 14a.

A clad portion, which surrounds a core of the optical fiber, is removed from the tip portion of the optical fiber that guides light emitted from the light source unit 13 to the puncture needle 14a. The clad 34 of the optical fiber is not removed between a portion of the optical fiber, which is connected to the light source unit 13, and the puncture needle body 31, and the clad 34 of the optical fiber is removed from a portion where the puncture needle body 31 and the optical fiber come into contact with each other so that the core is exposed to the outside. The core forms the light guide 32. The clad 34 does not need to be completely removed in the circumferential direction of the optical fiber, and only has to be removed from a portion of the optical fiber facing the puncture needle body 31.

In this embodiment, light is guided to the puncture needle 14a by using the optical fiber and the core of the optical fiber is used as the light guide 32 at the portion where the puncture needle body 31 and the optical fiber come into contact with each other, to emit light to the puncture needle body 31. According to this structure, it is possible to efficiently and stably guide light to the light guide. Other effects are the same as those of the first embodiment.

Figure 4A:
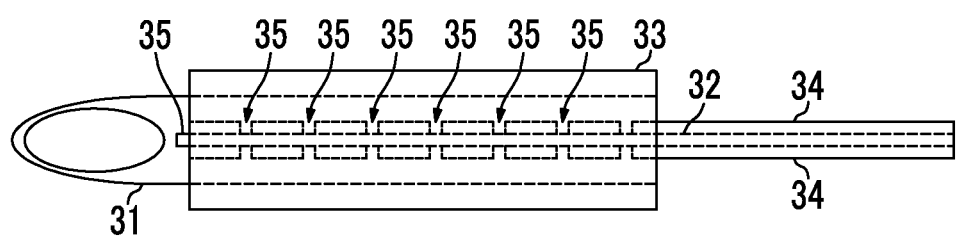
FIG. 4A is a top view of a puncture needle used in a third embodiment of the invention and FIG. 4B is a sectional view of a central portion of the puncture needle.
Figure 4B:
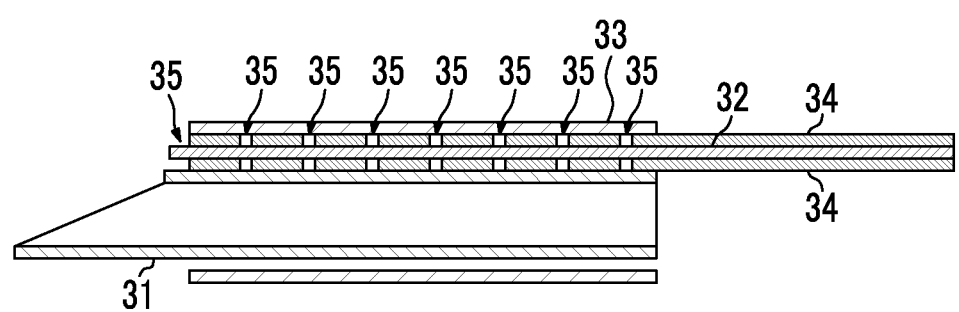

Next, a third embodiment of the invention will be described. FIG. 4A is a top view of a puncture needle used in the third embodiment of the invention and FIG. 4B is a sectional view of a central portion of the puncture needle. The third embodiment is different from the second embodiment shown in FIGS. 3A and 3B in that a clad 34 is not completely removed and is partially removed from a portion of a puncture needle 14b of this embodiment where a puncture needle body 31 and an optical fiber come into contact with each other.

In this embodiment, the clad 34 of the optical fiber is removed at a plurality of locations in an extension direction. For example, the clad 34 is removed at predetermined intervals, so that exposed portions 35 where a core (light guide 32) is exposed from the clad 34 are formed at predetermined intervals. Light is emitted to the puncture needle body 31 from the exposed portions 35 that are formed at the optical fiber. The exposed portions 35 do not need to be arranged at regular intervals in the extension direction of the optical fiber (the longitudinal direction of the puncture needle body 31). For example, the exposed portions may be arranged so that the interval between the exposed portions is reduced toward the tip of the puncture needle 14b.

In this embodiment, the clad 34 of the optical fiber, which guides light emitted from the light source unit 13 to the puncture needle 14b, is removed at a plurality of locations, so that a plurality of exposed portions 35 are formed in the longitudinal direction of the puncture needle 14b. A part of light, which travels through the light guide 32 toward the tip of the puncture needle 14b, leaks from the exposed portions 35 and is emitted to the puncture needle body 31. Since light is discretely irradiated to the puncture needle body 31 in this embodiment, photoacoustic waves can be discretely generated in the longitudinal direction of the puncture needle 14b. Other effects are the same as those of the second embodiment.

Figure 5A:
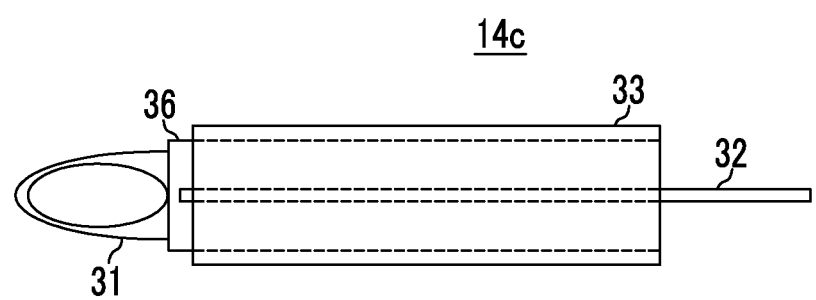
FIG. 5A is a top view of a puncture needle used in a fourth embodiment of the invention and FIG. 5B is a sectional view of a central portion of the puncture needle.
Figure 5B:
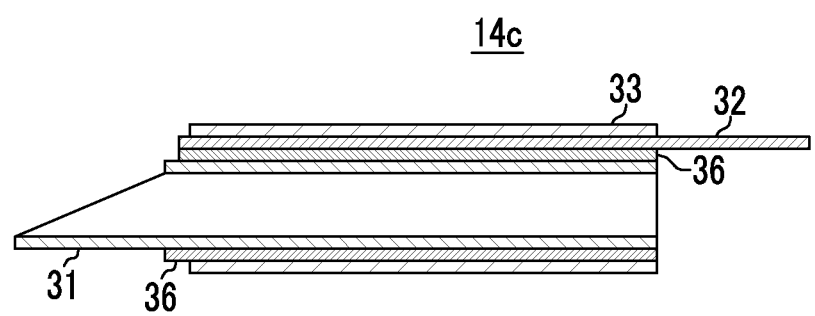

Subsequently, a fourth embodiment of the invention will be described. FIG. 5A is a top view of a puncture needle used in the fourth embodiment of the invention and FIG. 5B is a sectional view of a central portion of the puncture needle. The fourth embodiment is different from the first embodiment shown in FIGS. 2A and 2B in that a light guide 32 and a tube 33 are bonded to a puncture needle body 31 of a puncture needle 14c of this embodiment by an adhesive 36.

For example, the adhesive 36 is applied to the outer peripheral portion of the puncture needle body 31 and the light guide 32 and the tube 33 are bonded and fixed to the puncture needle body 31. An adhesive having light absorbency is used as the adhesive 36. For example, a black pigment is mixed to the adhesive 36. Light, which is emitted from the light guide 32 to the puncture needle body 31, is absorbed by the adhesive 36 having light absorbency, and photoacoustic waves are generated from the adhesive 36. The adhesive 36 does not necessarily need to be applied to the entire outer periphery of the puncture needle body 31, and only has to be applied to at least the periphery of the light guide 32.

In this embodiment, the light guide 32 and the tube 33 are fixed by the adhesive 36 having light absorbency. Since photoacoustic waves can be generated from the puncture needle body 31 and the adhesive 36 in this embodiment, photoacoustic waves can be efficiently generated. Other effects are the same as those of the first embodiment.

Figure 6A:
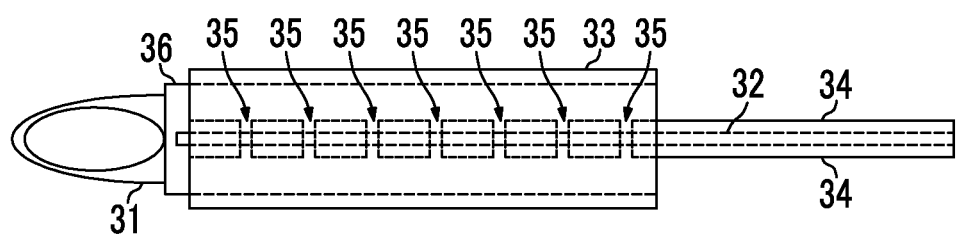
FIG. 6A is a top view of a puncture needle used in a fifth embodiment of the invention and FIG. 6B is a sectional view of a central portion of the puncture needle.
Figure 6B:
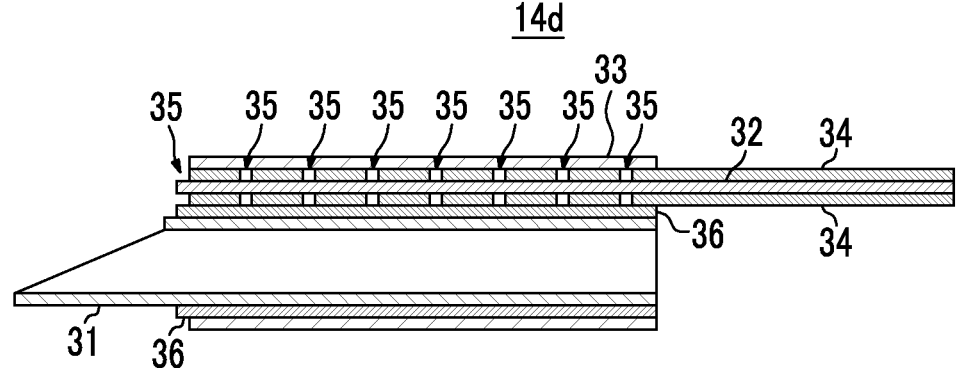

Next, a fifth embodiment of the invention will be described. FIG. 6A is a top view of a puncture needle used in the fifth embodiment of the invention and FIG. 6B is a sectional view of a central portion of the puncture needle. The fifth embodiment is different from the third embodiment shown in FIGS. 4A and 4B in that a light guide 32 and a tube 33 are bonded to a puncture needle body 31 of a puncture needle 14d of the invention by an adhesive 36. As in the fourth embodiment, an adhesive having light absorbency is used as the adhesive 36. Since the adhesive 36 having light absorbency is used, photoacoustic waves, which are discretely generated, can be strengthened in comparison with the third embodiment. Other effects are the same as those of the second embodiment.

Figure 7A:
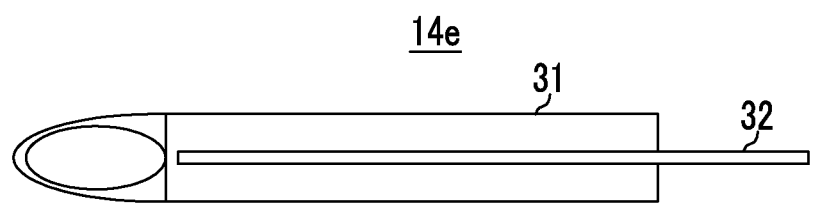
FIG. 7A is a top view of a puncture needle used in a sixth embodiment of the invention and FIG. 7B is a sectional view of a central portion of the puncture needle.
Figure 7B:
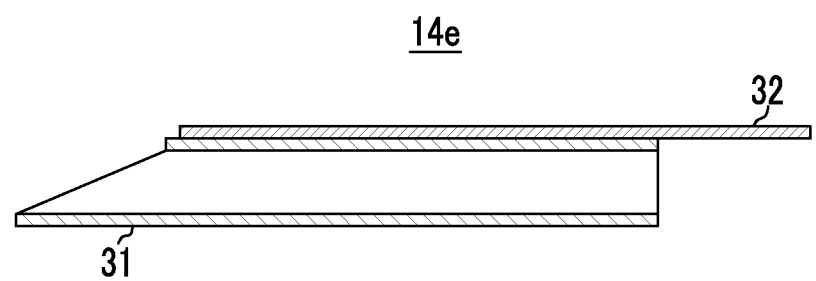

Further, a sixth embodiment of the invention will be described. FIG. 7A is a top view of a puncture needle used in the sixth embodiment of the invention and FIG. 7B is a sectional view of a central portion of the puncture needle. The sixth embodiment is different from the first embodiment in that a puncture needle 14e of this embodiment is not provided with the tube 33 (see FIGS. 2A and 2B). Others are the same as those of the first embodiment. Even in the case where the tube 33 is not provided, light can be emitted to a puncture needle body 31 from a light guide 32 in the longitudinal direction of a puncture needle body 31 as in the first embodiment. Accordingly, even in the case where the puncture needle 14e is stuck to a deep position, it is possible to confirm the position of the puncture needle 14e by using a photoacoustic image.

Figure 8A:
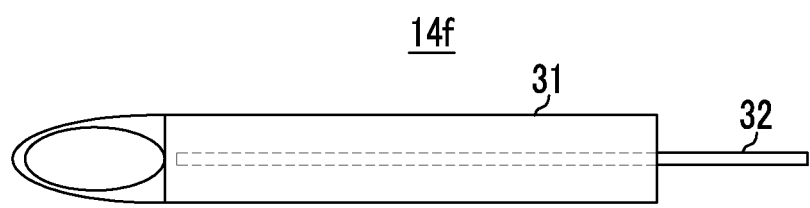
FIG. 8A is a top view of a puncture needle used in a seventh embodiment of the invention and FIG. 8B is a sectional view of a central portion of the puncture needle.
Figure 8B:
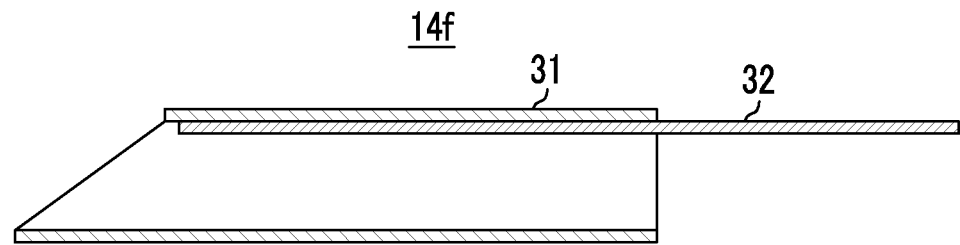

Subsequently, a seventh embodiment of the invention will be described. FIG. 8A is a top view of a puncture needle used in the seventh embodiment of the invention and FIG. 8B is a sectional view of a central portion of the puncture needle. The seventh embodiment is different from the sixth embodiment shown in FIGS. 7A and 7B in that a light guide 32 of a puncture needle 14f of this embodiment is disposed in a puncture needle body 31. Others may be the same as those of the sixth embodiment.

Since light is irradiated to an inner wall of the puncture needle body 31 from the light guide 32 in this embodiment, photoacoustic waves are mainly generated from the inner wall. Generally, the thickness of a metal plate of the puncture needle body 31 is sufficiently small, and photoacoustic waves generated from the inner wall are attenuated to some extent but can be sufficiently propagated in the subject. Since this embodiment is the same as the sixth embodiment except that the light guide 32 is mounted on an inner wall of the hollow shape puncture needle body 31, effects obtained from this embodiment are also the same as those obtained from the sixth embodiment.

Meanwhile, the above-mentioned respective embodiments can be appropriately combined. For example, the second embodiment in which the clad 34 of the optical fiber is removed from a portion of the puncture needle body 31 and the sixth embodiment from which the tube 33 covering the puncture needle body 31 and the light guide 32 is omitted may be combined with each other, and the tube 33 may be omitted in FIGS. 3A and 3B. Further, the third embodiment in which light is discretely irradiated to the puncture needle body 31 from the light guide 32 and the sixth embodiment may be combined with each other, and the tube 33 may be omitted in FIGS. 4A and 4B. Furthermore, the fourth embodiment using the adhesive 36 having light absorbency, the fifth embodiment, and the sixth embodiment may be combined, and the tube 33 may be omitted in each of FIGS. 5A and 5B and FIGS. 6A and 6B.

Moreover, in the seventh embodiment in which the light guide 32 is disposed in the puncture needle body 31, light may be guided to the puncture needle body 31 by the optical fiber as in the second embodiment (see FIGS. 3A and 3B), the clad 34 of the optical fiber may be removed at the puncture needle body 31 so that the core is exposed to the outside, and the core of the optical fiber may be used as the light guide 32. Further, in the seventh embodiment, the core of the optical fiber may be exposed to the outside at a plurality of locations in the longitudinal direction of the puncture needle body 31 as in the third embodiment (see FIGS. 4A and 4B) so that light is discretely irradiated to the puncture needle body 31 from the light guide 32.

Figure 9:
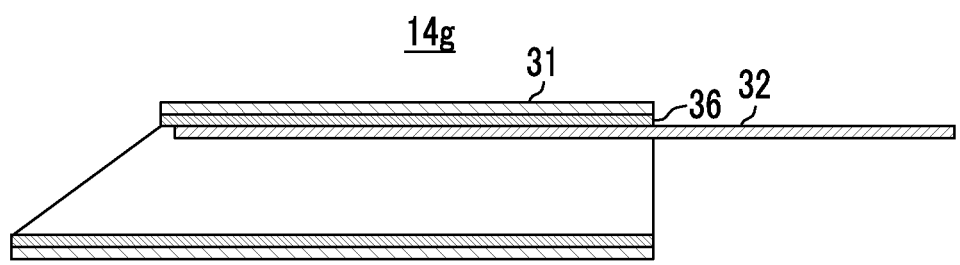
FIG. 9 is a sectional view of a central portion of a puncture needle according to a modification of the seventh embodiment.

Furthermore, as in the fourth embodiment, an adhesive having light absorbency can also be used in the seventh embodiment and a combination of the seventh embodiment and the first to third embodiments. FIG. 9 shows the section of a central portion of a puncture needle in which the fourth and seventh embodiments are combined with each other. In a puncture needle 14g according to a modification, an adhesive 36 having light absorbency is applied to the inner wall of the puncture needle body 31. The light guide 32 is bonded and fixed to the inner wall of the puncture needle body 31 by the adhesive 36. The adhesive 36 does not need to be applied to the entire inner wall of the puncture needle body 31, and only has to be applied to at least a portion of the inner wall of the puncture needle body to which the light guide 32 is bonded and fixed.

An example in which end face treatment is not performed at the tip portion of the light guide 32 has been described in each of the above-mentioned embodiments, but any end face treatment can be performed at the tip portion. For example, in FIG. 2B, the tip of the light guide 32 and the tip of the puncture needle 14 may be obliquely cut at the same angle and in the same direction. In this case, since light emitted from the tip of the light guide is directed to the puncture needle body 31, photoacoustic signals generated from the tip portion can be strengthened. In the case where the light guide 32 is disposed in the puncture needle body 31 as in the seventh embodiment, the end of the light guide 32 and the end of the puncture needle 14 need to be cut in a direction opposite to the direction of the case in which the light guide 32 is disposed outside the puncture needle body 31.

The invention has been described above on the basis of the preferred embodiments thereof. However, the photoacoustic image generating device and the puncture needle of the invention are not limited to only the above-mentioned embodiments, and various alterations and modifications formed from the structures of the above-mentioned embodiments are also included in the scope of the invention.

What is claimed is:

1. A puncture needle comprising:
   a hollow puncture needle body that has an opening formed at a tip thereof;
   a light guide that extends in a longitudinal direction of the hollow puncture needle body and emits light at least in part to the hollow puncture needle body while guiding light emitted from a light source toward the tip of the hollow puncture needle body; and
   a tube that covers the hollow puncture needle body and the light guide,
   wherein the hollow puncture needle body is metal,
   wherein the light guide is disposed outside the hollow puncture needle body,
   wherein the tube has a property that allows acoustic waves to be transmitted,
   wherein the light guide is bonded to the hollow puncture needle body by an adhesive having light absorbency,
   wherein the light guide includes an optical fiber of which a clad of at least a part of a portion coming into contact with the hollow puncture needle body is removed, and
   wherein the adhesive generates photoacoustic waves when the adhesive absorbs the guiding light.

2. The puncture needle according to claim 1, wherein the tube is made of a fluorine resin.

3. The puncture needle according to claim 1, wherein the clad is removed at a plurality of locations in the longitudinal direction of the hollow puncture needle body.

4. The puncture needle according to claim 3, wherein the clad is removed at predetermined intervals.

5. The puncture needle according to claim 1, wherein the optical fiber is a part of an optical wire that guides the light emitted from the light source to the hollow puncture needle body.

6. A photoacoustic image generating device comprising:
   the puncture needle according to claim 1;
   the light source;
   a probe that detects a photoacoustic wave generated in a subject after the light is emitted from the light guide; and
   a processor configured to generate a photoacoustic image on the basis of a detection signal of the photoacoustic wave.

* * * * *